(12) United States Patent
Abdolahad et al.

(10) Patent No.: US 11,867,649 B2
(45) Date of Patent: Jan. 9, 2024

(54) ELECTROCHEMICAL LIPIDOMICS FOR CANCER DIAGNOSIS

(71) Applicants: Mohammad Abdolahad, Tehran (IR); Ashkan Zandi, Tehran (IR)

(72) Inventors: Mohammad Abdolahad, Tehran (IR); Ashkan Zandi, Tehran (IR)

(73) Assignee: NANO HESGARSAZAN SALAMAT ARYA INCUBATION CENTER FOR MEDICALEQUIPMENT AND DEVICES, Tehran (IR)

( * ) Notice: Subject to any disclaimer, the term of this patent is extended or adjusted under 35 U.S.C. 154(b) by 786 days.

(21) Appl. No.: 16/654,174

(22) Filed: Oct. 16, 2019

(65) Prior Publication Data

US 2020/0049641 A1   Feb. 13, 2020

Related U.S. Application Data

(60) Provisional application No. 62/746,605, filed on Oct. 17, 2018.

(51) Int. Cl.
*G01N 27/02*   (2006.01)
*G01N 33/487*   (2006.01)
(Continued)

(52) U.S. Cl.
CPC ..... *G01N 27/026* (2013.01); *G01N 33/48707* (2013.01); *G01R 27/22* (2013.01);
(Continued)

(58) Field of Classification Search
CPC ........... G01N 33/48707; G01N 27/026; G01N 2800/7028; B82Y 5/00; B82Y 40/00; B82Y 30/00; G01R 31/2812; G01R 27/22
See application file for complete search history.

(56) References Cited

U.S. PATENT DOCUMENTS

2009/0289213 A1* 11/2009 Pipper .................... C07K 1/22
  252/62.51 R
2012/0234694 A1*  9/2012 Vecitis ............... B01D 39/2055
  204/264

(Continued)

OTHER PUBLICATIONS

Han et al.2007. Quantification of the Heterogeneity in Breast Cancer Cell Lines Using VWhole-Cell Impedance Spectroscopy.*
(Continued)

*Primary Examiner* — Rebecca M Fritchman
(74) *Attorney, Agent, or Firm* — Bawa IP Law Firm; Haris Zaheer Bajwa

(57) ABSTRACT

A method for detecting cancerous status of a biological sample. The method includes calculating a charge transfer resistance ($R_{ct}$) of an electrochemical impedance spectroscopy (EIS) associated with lipid secretion of a biological sample, detecting a cancerous state for the biological sample responsive to the calculated $R_{ct}$ being equal to or more than a threshold value, and detecting a normal state for the biological sample responsive to the calculated $R_{ct}$ being less than the threshold value. The biological sample includes a biological sample suspected to be cancerous.

17 Claims, 16 Drawing Sheets

(51) Int. Cl.
  *G01R 31/28* (2006.01)
  *G01R 27/22* (2006.01)
  *B82Y 5/00* (2011.01)
  *B82Y 30/00* (2011.01)
  *B82Y 40/00* (2011.01)

(52) U.S. Cl.
  CPC .......... *G01R 31/2812* (2013.01); *B82Y 40/00* (2013.01); *G01N 2800/7028* (2013.01)

(56) References Cited

U.S. PATENT DOCUMENTS

2017/0244110 A1* 8/2017 Abdolahad ...... G01N 33/54373
2018/0292400 A1* 10/2018 Kumta ............... G01N 33/6887
2019/0002948 A1* 1/2019 Ferapontova ........ C12Q 1/6825

OTHER PUBLICATIONS

Abdolahad. 2013.Single cell resolution diagnosis of cancer by carbon nanotube electrical spectroscopy. 2013 in Nanoscale 5: 3421-3427.*
Chornukur in Impedance-Based Miniaturized Biosensor for Ultrasensitive and Fast Prostate-Specific Antigen Detection (Year: 2011).*

* cited by examiner

ELECTROCHEMICAL LIPIDOMICS FOR CANCER DIAGNOSIS

CROSS-REFERENCE TO RELATED APPLICATION

This application claims the benefit of priority from U.S. Provisional Patent Application Ser. No. 62/746,605 filed on Oct. 17, 2018, and entitled "ELECTROCHEMICAL LIPIDOMICS FOR CANCER DIAGNOSIS", which is incorporated herein by reference in its entirety.

TECHNICAL FIELD

The present disclosure generally relates to cancer diagnosis, and particularly, to a nanoelectrochemical cell free approach using electrochemical impedance spectroscopy (EIS) to detect cancerous samples based on tracing the secreted lipids from a biopsied sample of a tissue.

BACKGROUND

A challenge in achieving precise diagnosis of cancer is applying external biomarkers that represent useful data from the function of disease meanwhile tumor micro-environment contains secretomes as a rich source of cancer associated macromolecules with protein, lipid and ionic natures. However, secretome analysis to trace such tumor markers requires use of complicated methods with analytical challenges and non-desired bindings in detecting the true cancer markers.

Among the secretion components, lipids are one of the crucial biomarkers. Cancer is the consequence of an alteration in lipid metabolic enzymes and pathways as far as lipid induced facilitation of metastasis become interested for cancer biologists. Cancer cells show an increased lipogenesis secreted to mediate some invasive associated pathways such as angiogenesis, immune suppressing and chemoresistance. Hence, lipids are now considered as hallmarks of cancer aggressiveness.

Hence, there is a need for a highly accurate method for cancer diagnosis via tracing lipid secretion from suspicious cell lines and biopsied samples from patients. Additionally, there is a need for a method for cancer diagnosis that should be fast, simple, and practically applicable instead of complicated methods utilizing bio-markers and long-term pathology tests. Moreover, there is a need for a cell-free method and sensor for cancer diagnosis based on lipid secretion of tissue samples instead of cell-based methods and sensors.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for detecting cancerous status of a biological sample. The method may include calculating a charge transfer resistance ($R_{ct}$) of an electrochemical impedance spectroscopy (EIS) associated with lipid secretion of a biological sample, detecting a cancerous state for the biological sample responsive to the calculated $R_{ct}$ being equal to or more than a threshold value, and detecting a normal state for the biological sample responsive to the calculated $R_{ct}$ being less than the threshold value. The biological sample may include a biological sample suspected to be cancerous.

In an exemplary implementation, each of the detecting the cancerous state for the biological sample and the detecting the normal state for the biological sample may include comparing the calculated $R_{ct}$ with the threshold value.

In an exemplary implementation, calculating the $R_{ct}$ of the EIS associated with the lipid secretion of the biological sample may include dropping peripheral aqueous media of the biological sample on an array of hydrophobic conductive nanostructures grown on three-integrated electrodes of a biosensor, recording the EIS of the dropped peripheral aqueous media of the biological sample on the array of hydrophobic conductive nanostructures using an electrochemical analyzer, and measuring a diameter of a semicircular curve of the recorded EIS. The peripheral aqueous media of the biological sample may include the lipid secretion of the biological sample.

In an exemplary implementation, dropping the peripheral aqueous media of the biological sample on the array of hydrophobic conductive nanostructures grown on the three-integrated electrodes of the biosensor may include dropping the peripheral aqueous media of at least one of a plurality of biological cells, a plurality of biological cell lines, a part of a tissue obtained through surgery or biopsy, a lipid phase of the biological sample, and combinations thereof on the array of hydrophobic conductive nanostructures grown on the three-integrated electrodes of the biosensor.

In an exemplary implementation, dropping the peripheral aqueous media of the biological sample on the array of hydrophobic conductive nanostructures grown on the three-integrated electrodes of the biosensor may include forming a mixture of the biological sample and a solution of metal ions by mixing the biological sample with the solution of metal ions, and placing the mixture of the biological sample and the solution of metal ions on the hydrophobic conductive nanostructures array grown on the three-integrated electrodes of the biosensor.

In an exemplary implementation, dropping the peripheral aqueous media of the biological sample on the array of hydrophobic conductive nanostructures grown on the three-integrated electrodes of the biosensor may include dropping an extracted lipid phase of the biological sample on the array of hydrophobic conductive nanostructures grown on the three-integrated electrodes of the biosensor. In an exemplary implementation, dropping the peripheral aqueous media of the biological sample on the array of hydrophobic conductive nanostructures grown on the three-integrated electrodes of the biosensor may include extracting a lipid phase from the biological sample, forming a mixture of the extracted lipid phase and a solution of metal ions by mixing the extracted lipid phase with the solution of metal ions, and placing the mixture of the extracted lipid phase and the solution of metal ions on the hydrophobic conductive nanostructures array grown on the three-integrated electrodes of the biosensor.

In an exemplary implementation, extracting the lipid phase from the biological sample may include forming a two-phase mixture of the biological sample in a solution of chloroform and methanol, separating a bottom fraction of the two-phase mixture, and drying the separated bottom fraction of the two-phase mixture. In an exemplary implementation, forming the two-phase mixture of the biological sample in the solution of chloroform and methanol may include culturing the biological sample in a cell culture media, and adding a solution of chloroform and methanol to the cultured biological sample by adding an equal volume of the solution of chloroform and methanol with a volume ratio of 1:2 (Chloroform:methanol) to the biological sample. In another exemplary implementation, forming the two-phase mixture of the biological sample in the solution of chloroform and methanol may include absorbing secretion of the biological sample by keeping the biological sample on a foam for a time period between 5 minutes and 30 minutes, forming a mixture of chloroform and the secretion of the biological sample by putting the foam containing the secretion of the biological sample in a chloroform solution inside a shaker for a time period between 5 minutes and 30 minutes, removing the foam the mixture of chloroform and the secretion of the biological sample, and adding methanol to mixture of chloroform and the secretion of the biological sample with a volume ratio of 1:2 (Chloroform:methanol).

In an exemplary implementation, dropping the peripheral aqueous media of the biological sample on the array of hydrophobic conductive nanostructures grown on the three-integrated electrodes of the biosensor may include dropping the peripheral aqueous media of the biological sample on an array of vertically aligned multi-walled carbon nanotubes (VAMWCNTs) grown on the three-integrated electrodes of the biosensor. In an exemplary implementation, dropping the peripheral aqueous media of the biological sample on the array of VAMWCNTs grown on the three-integrated electrodes of the biosensor may include dropping the peripheral aqueous media of the biological sample on the array of VAMWCNTs with a length between 2 μm and 12 μm and a diameter between 20 nm and 75 nm for each VAMWCNT of the array of VAMWCNTs.

In an exemplary implementation, recording the EIS of the dropped peripheral aqueous media of the biological sample on the array of hydrophobic conductive nanostructures using the electrochemical analyzer may include recording the EIS from the dropped peripheral aqueous media of the biological sample on the array of hydrophobic conductive nanostructures at a AC voltage between 5 mV and 10 mV by sweeping a plurality of frequency values between 0.01 Hz and 100 kHz.

In an exemplary implementation, calculating the $R_{ct}$ of the EIS associated with the lipid secretion of the biological sample may further include fabricating the biosensor by growing the array of hydrophobic conductive nanostructures on the three-integrated electrodes patterned on a catalyst layer deposited on a substrate. In an exemplary embodiment, the substrate may include at least one of a glass substrate, a silicon substrate, a ceramic substrate, and combinations thereof, and the catalyst layer may include a layer of at least one of iron, cobalt, nickel, and combinations thereof.

In an exemplary implementation, fabricating the biosensor may include depositing the catalyst layer on the substrate by thermally growing the catalyst layer on the substrate, patterning the three-integrated electrodes on the catalyst layer using photolithography technique, and growing the array of hydrophobic conductive nanostructures on the patterned three-integrated electrodes using a direct-current plasma enhanced chemical vapor deposition (DC-PECVD) technique. Where, the three-integrated electrodes may include a working electrode, a counter electrode, and a reference electrode.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1:
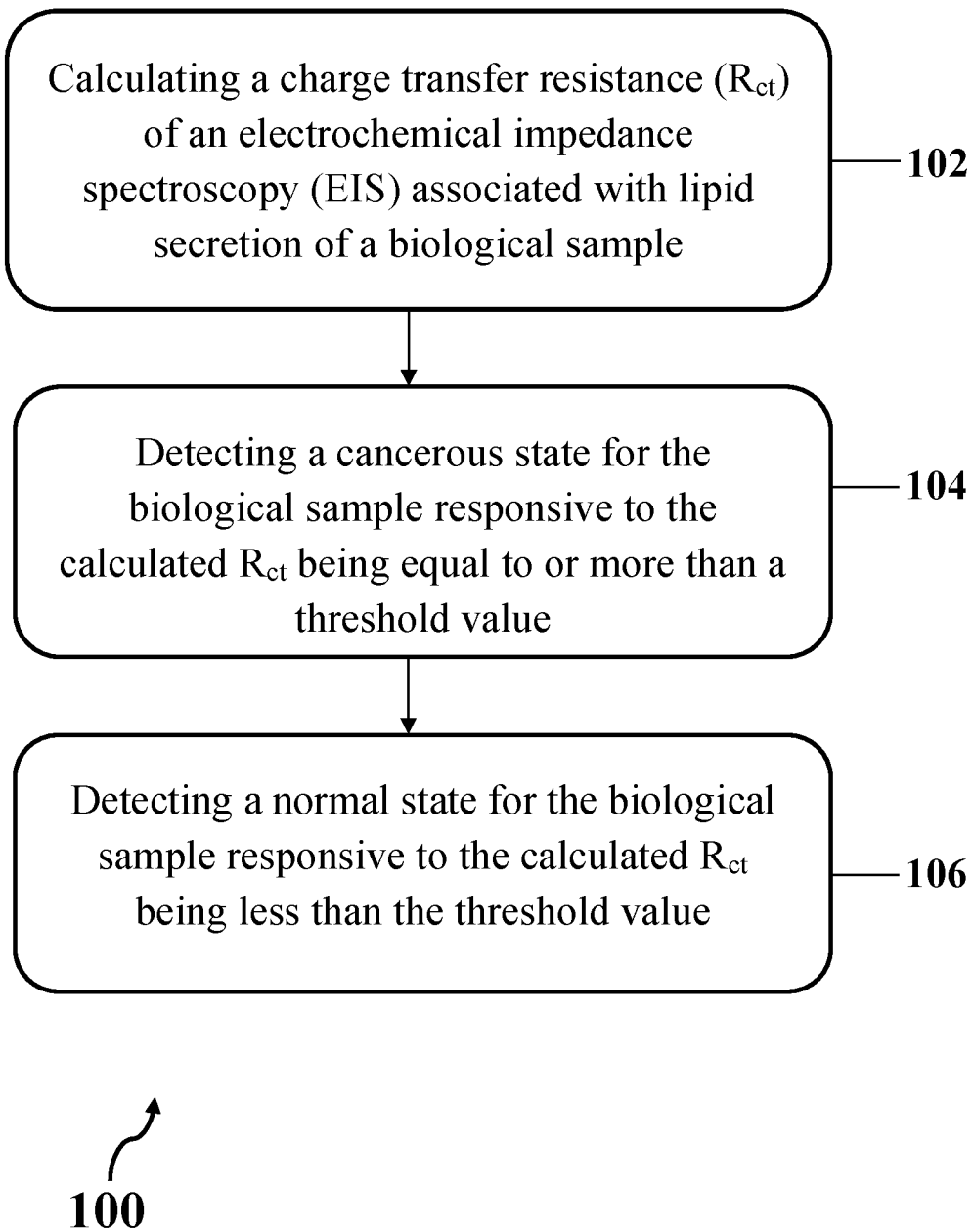
FIG. 1 illustrates an exemplary method for detecting cancerous status of a biological sample, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

In an exemplary embodiment, lipids may play an important role in mediating crosstalk between cancer cells in tumor stroma. Progression in malignant phenotypes may exhibit strong correlation with increased level of lipids secreted from cancer cells. In addition, lipids may be considered as dielectric components in conductive biological media. The electrically insulating behavior of the lipids may be much stronger than other contents of intercostal and intercellular fluids.

Herein, an exemplary nanoelectrochemical cell free approach by impedance spectroscopy is disclosed that may be designed and utilized to detect cancerous samples based on tracing secreted lipids from cancer and normal samples (or cells). Accordingly, an exemplary cell-free dielectric spectroscopic method utilizing an exemplary electrochemical biosensor with three-integrated electrodes coated by a super hydrophobic electrically conductive material, such as multiwall carbon nanotube arrays (MWCNTs) may be applied to investigate the concentration of secreted lipids from the cell lines as well as biopsy samples of the patients, which may be suspicious to cancer. The exemplary MWCNTs as highly electrically conductive nanostructures with super hydrophobic properties may facilitate the perfect physical and electrical interaction between the lipids of secretion droplet and the surface of the electrodes of the exemplary electrochemical biosensor. Herein, the dielectric response of cells' secretion that may include an electrochemical impedance spectroscopy (EIS) may be compared to cells' phenotypes for any probable correlation in cancer diagnosis. The exemplary super hydrophobic electrically conductive material may form highly sensitive electrodes for EIS measurements.

FIG. 1 shows exemplary method 100 for detecting cancerous status of a biological sample, consistent with one or more exemplary embodiments of the present disclosure. Exemplary method 100 may include calculating a charge transfer resistance ($R_{ct}$) of an electrochemical impedance spectroscopy (EIS) associated with lipid secretion of a biological sample (step 102), detecting a cancerous state for the biological sample responsive to the calculated $R_{ct}$ being equal to or more than a threshold value (step 104), and detecting a normal state for the biological sample responsive to the calculated $R_{ct}$ being less than the threshold value (step 106). In an exemplary embodiment, the biological sample may include a biological sample suspected to be cancerous. In an exemplary embodiment, the lipid secretion of the biological sample may include a portion or whole of lipid content of the biological sample that may be extracted from the biological sample.

Figure 2:
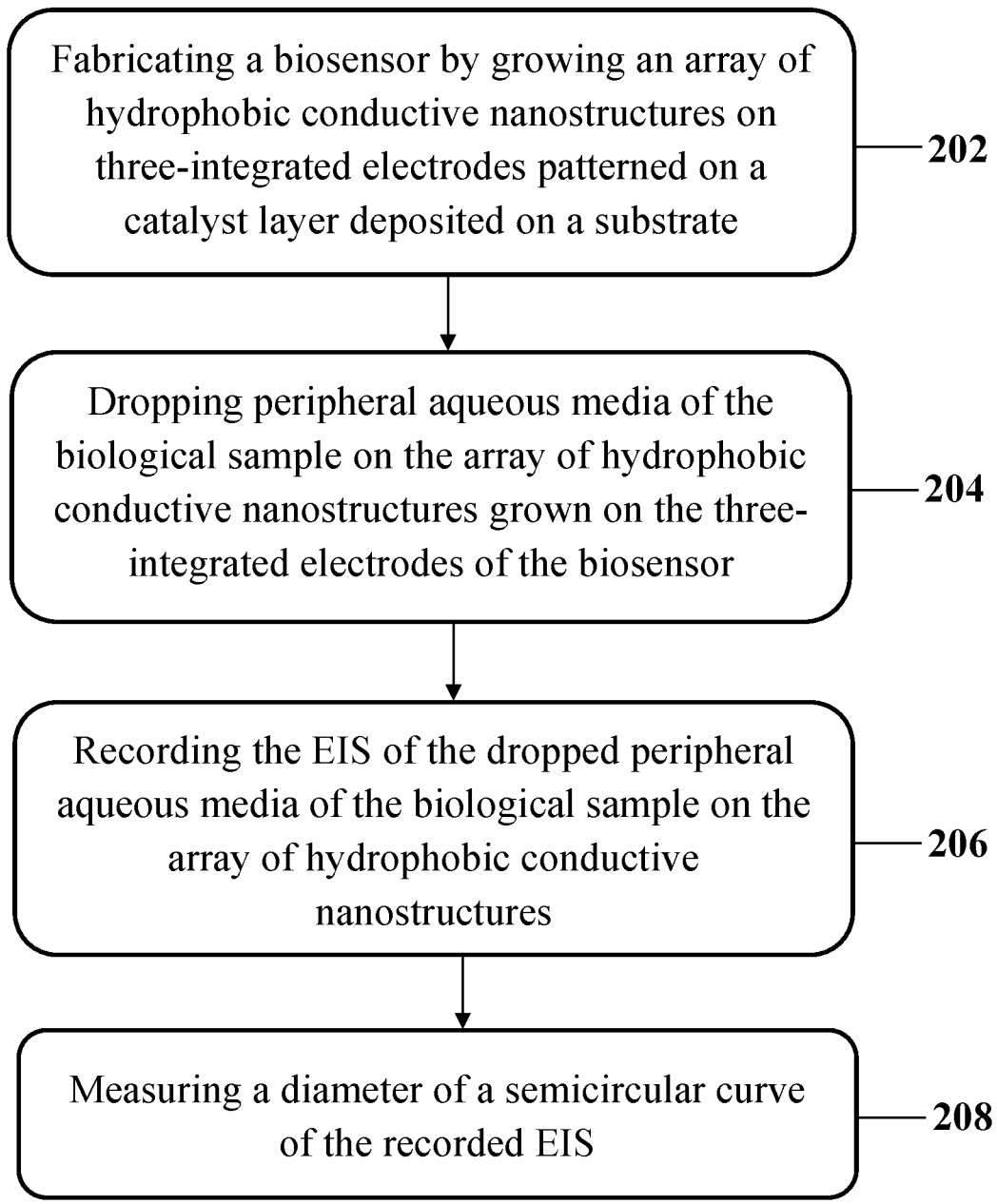
FIG. 2 illustrates an exemplary implementation of calculating the charge transfer resistance ($R_{ct}$) of the electrochemical impedance spectroscopy (EIS) associated with lipid secretion of the biological sample, consistent with one or more exemplary embodiments of the present disclosure.

In detail, step 102 may include calculating a $R_{ct}$ of an EIS associated with lipid secretion of the biological sample. FIG. 2 shows an exemplary implementation of calculating the $R_{ct}$ of the EIS associated with lipid secretion of the biological sample (step 102), consistent with one or more exemplary embodiments of the present disclosure. In an exemplary implementation, calculating the $R_{ct}$ of the EIS associated with lipid secretion of the biological sample (step 102) may include dropping peripheral aqueous media of the biological sample on an array of hydrophobic conductive nanostructures grown on three-integrated electrodes of a biosensor (step 204), recording the EIS of the dropped peripheral aqueous media of the biological sample on the array of hydrophobic conductive nanostructures using an electrochemical analyzer (step 206), and measuring a diameter of a semicircular curve of the recorded EIS (step 208). In an exemplary embodiment, the peripheral aqueous media of the biological sample may include secretion of the biological sample. The peripheral aqueous media of the biological sample may include the lipid secretion (lipid content) of the biological sample.

In another exemplary implementation, calculating the $R_{ct}$ of the EIS associated with lipid secretion of the biological sample (step 102) may further include fabricating the biosensor by growing the array of hydrophobic conductive nanostructures on the three-integrated electrodes patterned on a catalyst layer deposited on a substrate (step 202). In an exemplary implementation, fabricating the biosensor by growing the array of hydrophobic conductive nanostructures on the three-integrated electrodes patterned on the catalyst layer deposited on the substrate (step 202) may include depositing the catalyst layer on the substrate by thermally growing the catalyst layer on the substrate, patterning the three-integrated electrodes on the catalyst layer using photolithography technique, and growing the array of hydrophobic conductive nanostructures on the patterned three-integrated electrodes using a direct-current plasma enhanced chemical vapor deposition (DC-PECVD) technique in a DC-PECVD reactor. In an exemplary embodiment, the array of hydrophobic conductive nanostructures may include an array of multi-walled carbon nanotubes (MWCNTs), for example, an array of vertically aligned multi-walled carbon nanotubes (VAMWCNTs).

Figure 3:
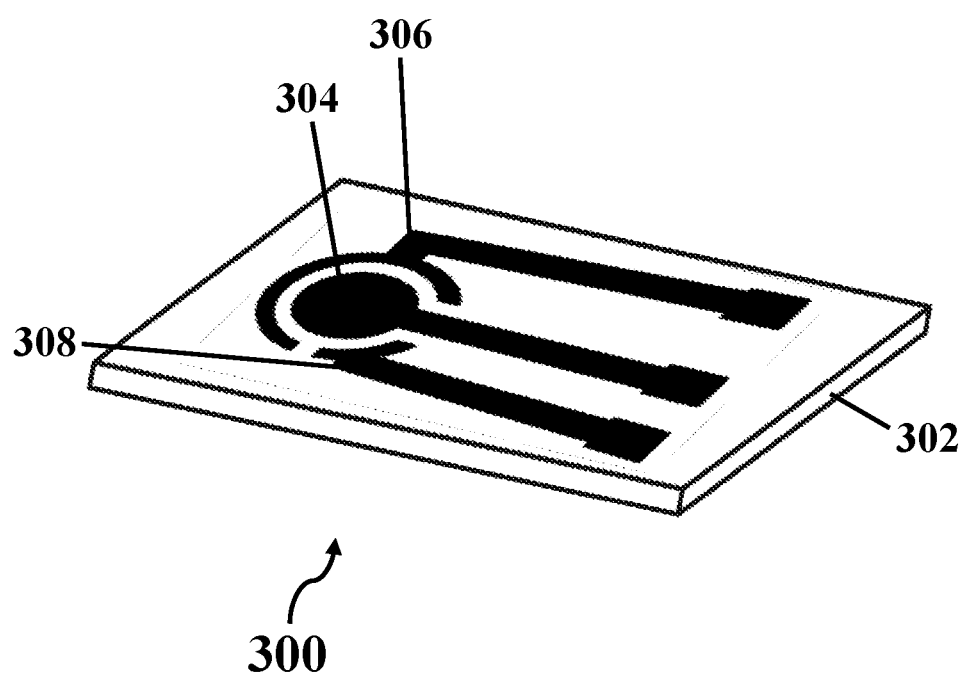
FIG. 3 illustrates a schematic view of an exemplary biosensor, consistent with one or more exemplary embodiments of the present disclosure.

FIG. 3 shows a schematic view of exemplary biosensor 300, consistent with one or more exemplary embodiments of the present disclosure. Exemplary biosensor 300 may be fabricated by growing an array of hydrophobic conductive nanostructures on a three-integrated electrodes patterned on a catalyst layer deposited on a substrate (step 202). Exemplary biosensor 300 may include exemplary substrate 302 and exemplary three-integrated electrodes that may include exemplary working electrode 304, exemplary counter electrode 306, and reference electrode 308. Accordingly, the array of hydrophobic conductive nanostructures may be grown on surface of exemplary working electrode 304, exemplary counter electrode 306, and exemplary reference electrode 308.

In an exemplary embodiment, working electrode 304 may have a circular shape and counter electrode 306 may have a ring shape around working electrode 304 in order to increase a resolution of the EIS that may be recorded using exemplary biosensor 300 that may be connected to an exemplary electrochemical analyzer.

In an exemplary embodiment, exemplary substrate 302 may include a substrate, on which a hydrophobic conductive material may be coated and patterned. In an exemplary embodiment, exemplary substrate 302 may include at least one of a glass substrate, a silicon substrate, a ceramic substrate, and combinations thereof. The silicon substrate may include a silicon substrate with a layer of silicon dioxide ($SiO_2$) deposited thereon. In an exemplary embodiment, the catalyst layer may include a layer of a catalyst for growing the hydrophobic conductive nanostructures thereon that may include a layer of at least one of iron, cobalt, nickel, and combinations thereof. In an exemplary embodiment, the array of hydrophobic conductive nanostructures grown on the three-integrated electrodes of exemplary biosensor 300 may include an array of VAMWCNTs with a length between about 2 μm and about 12 μm, and a diameter between about 20 nm and about 75 nm for each VAMWCNT of the array of VAMWCNTs.

Referring again to FIG. 2, calculating the $R_{ct}$ of the EIS associated with the lipid secretion of the biological sample (step 102 of exemplary method 100) may further include dropping peripheral aqueous media of the biological sample on the array of hydrophobic conductive nanostructures grown on the three-integrated electrodes of the biosensor that may include exemplary biosensor 300 (step 204). In an exemplary implementation, dropping the peripheral aqueous media of the biological sample on the array of hydrophobic conductive nanostructures grown on the three-integrated electrodes of exemplary biosensor 300 may include placing the biological sample on the array of hydrophobic conductive nanostructures by placing the biological sample on exemplary biosensor 300. In an exemplary implementation, dropping the peripheral aqueous media of the biological sample on the array of hydrophobic conductive nanostructures grown on the three-integrated electrodes of the biosensor may include dropping the peripheral aqueous media of the biological sample on an array of VAMWCNTs grown on the three-integrated electrodes of the biosensor.

In an exemplary implementation, dropping the peripheral aqueous media of the biological sample on the array of hydrophobic conductive nanostructures grown on the three-integrated electrodes of exemplary biosensor 300 (step 204) may include dropping the peripheral aqueous media of at least one of a plurality of biological cells, a plurality of biological cell lines, a part of a tissue obtained through surgery or biopsy, a lipid phase of the biological sample, and combinations thereof, on the array of hydrophobic conductive nanostructures grown on the three-integrated electrodes of exemplary biosensor 300. In an exemplary embodiment, the biological sample may include at least one of a plurality of biological cells, a portion of a tissue, a biopsied sample from a patient, a biopsied sample from a tumor, and combinations thereof. In an exemplary embodiment, the biological sample may include a biological sample suspected to be cancerous that may be examined utilizing exemplary method 100 for detecting presence of cancer. In an exemplary implementation, method 100 may be utilized for detecting the presence of at least one of breast cancer, kidney cancer, ovarian cancer, prostate cancer, skin cancer, colon cancer, stomach cancer, and combinations thereof in the biological sample.

In an exemplary implementation, dropping the peripheral aqueous media of the biological sample on the array of hydrophobic conductive nanostructures grown on the three-integrated electrodes of exemplary biosensor 300 (step 204) may include dropping whole secretion of the biological sample on the array of hydrophobic conductive nanostructures grown on the three-integrated electrodes of exemplary biosensor 300. In another exemplary implementation, dropping the peripheral aqueous media of the biological sample on the array of hydrophobic conductive nanostructures grown on the three-integrated electrodes of exemplary biosensor 300 (step 204) may include dropping a lipid phase of the secretion of the biological sample, that may be derived from the biological sample, on the array of hydrophobic conductive nanostructures grown on the three-integrated electrodes of exemplary biosensor 300.

Figure 4A:
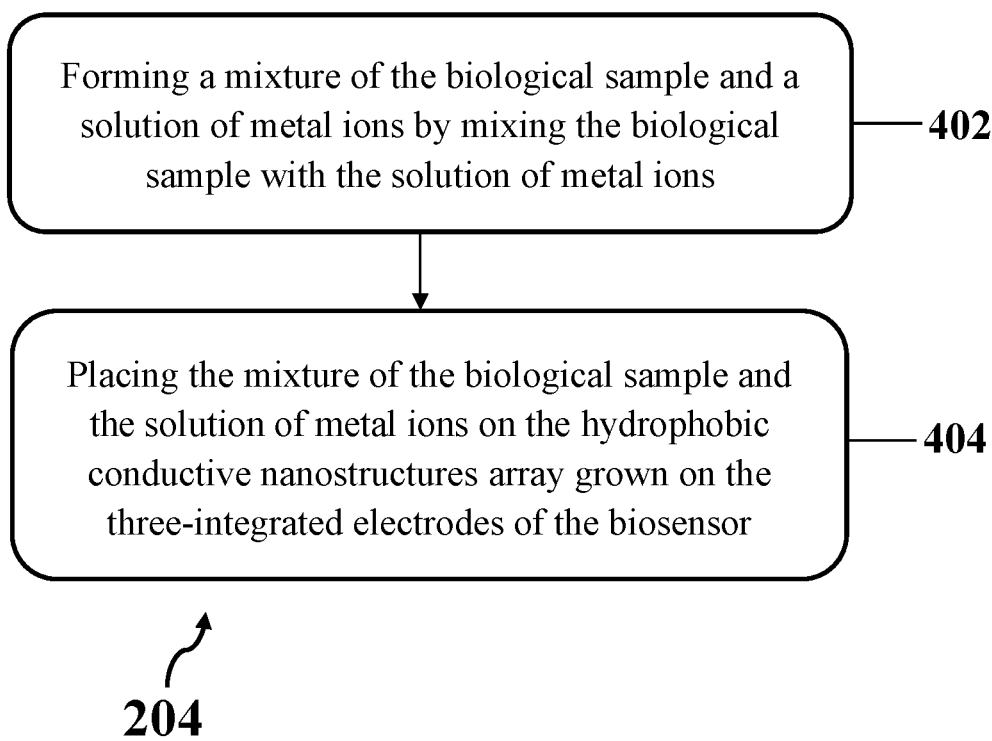
FIG. 4A illustrates an exemplary implementation of dropping the peripheral aqueous media of the biological sample on the array of hydrophobic conductive nanostructures grown on the three-integrated electrodes of an exemplary biosensor, consistent with one or more exemplary embodiments of the present disclosure.

FIG. 4A shows an exemplary implementation of dropping the peripheral aqueous media of the biological sample on the array of hydrophobic conductive nanostructures grown on the three-integrated electrodes of exemplary biosensor 300 (step 204), consistent with one or more exemplary embodiments of the present disclosure. Accordingly, dropping the peripheral aqueous media of the biological sample on the array of hydrophobic conductive nanostructures grown on the three-integrated electrodes of exemplary biosensor 300 may include forming a mixture of the biological sample and a solution of metal ions by mixing the biological sample with the solution of metal ions (step 402), and placing the mixture of the biological sample and the solution of metal ions on the hydrophobic conductive nanostructures array grown on the three-integrated electrodes of exemplary biosensor 300 (step 404). In some implementations, dropping the peripheral aqueous media of the biological sample on the array of hydrophobic conductive nanostructures grown on the three-integrated electrodes of exemplary biosensor 300 may include an individual step of placing the biological sample and the solution of metal ions on the hydrophobic conductive nanostructures array grown on the three-integrated electrodes of exemplary biosensor 300.

Figure 4B:
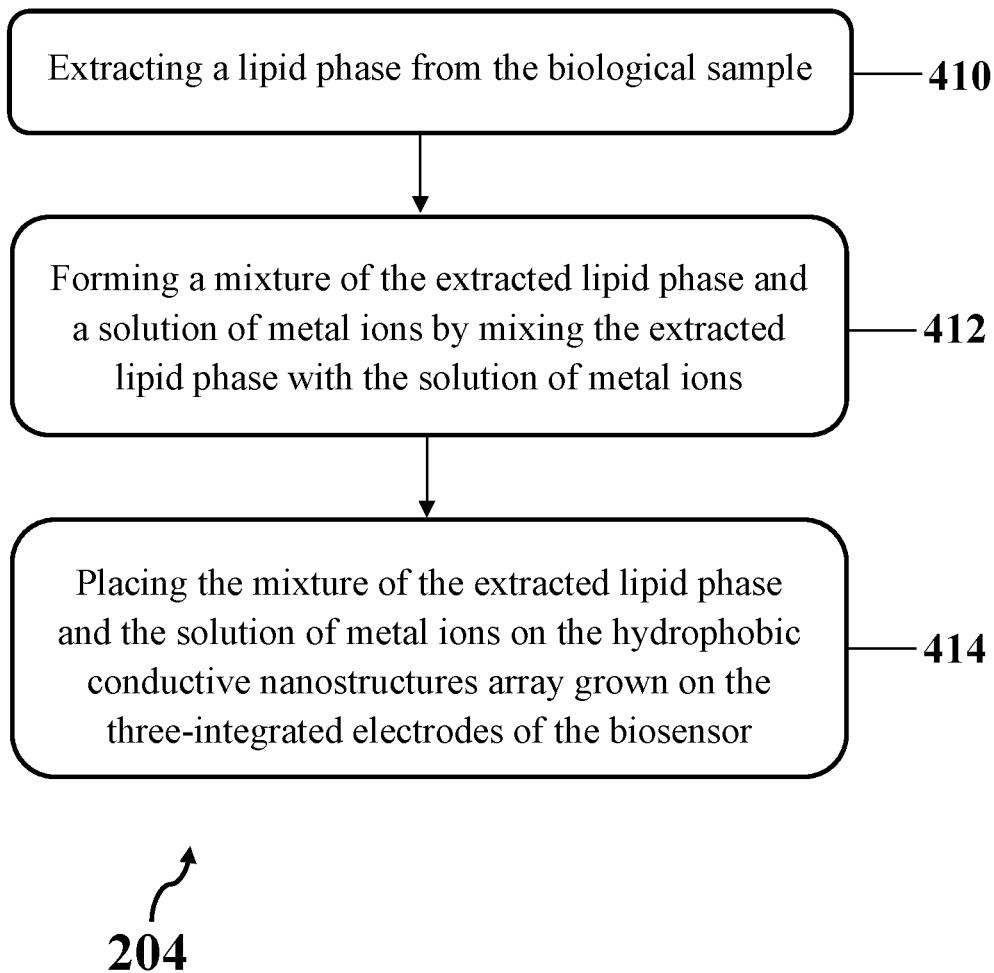
FIG. 4B illustrates another exemplary implementation of dropping the peripheral aqueous media of the biological sample on the array of hydrophobic conductive nanostructures grown on the three-integrated electrodes of an exemplary biosensor, consistent with one or more exemplary embodiments of the present disclosure.

FIG. 4B shows another exemplary implementation of dropping the peripheral aqueous media of the biological sample on the array of hydrophobic conductive nanostructures grown on the three-integrated electrodes of exemplary biosensor 300 (step 204), consistent with one or more exemplary embodiments of the present disclosure. In such exemplary implementation, dropping the peripheral aqueous media of the biological sample on the array of hydrophobic conductive nanostructures grown on the three-integrated electrodes of exemplary biosensor 300 (step 204) may include dropping an extracted lipid phase of the biological sample on the array of hydrophobic conductive nanostructures grown on the three-integrated electrodes of the biosensor. Accordingly, dropping the peripheral aqueous media of the biological sample on the array of hydrophobic conductive nanostructures grown on the three-integrated electrodes of exemplary biosensor 300 may include extracting a lipid phase from the biological sample (step 410), forming a mixture of the extracted lipid phase and a solution of metal ions by mixing the extracted lipid phase with the solution of metal ions (step 412), and placing the mixture of the extracted lipid phase and the solution of metal ions on the hydrophobic conductive nanostructures array grown on the three-integrated electrodes of exemplary biosensor 300 (step 414). In some implementations, dropping the peripheral aqueous media of the biological sample on the array of hydrophobic conductive nanostructures grown on the three-integrated electrodes of exemplary biosensor 300 may include extracting the lipid phase from the biological sample (step 410), and directly placing the extracted lipid phase on the hydrophobic conductive nanostructures array grown on the three-integrated electrodes of exemplary biosensor 300.

In an exemplary embodiment, the solution of metal ions may include a solution containing one or more metal ions. In an exemplary embodiment, the solution of metal ions may include a solution of potassium ferricyanide ($K_3Fe(CN)_6$ and/or $K_4Fe(CN)_6$) with a concentration of about 5 mM of the potassium ferricyanide in water.

In an exemplary implementation, placing the mixture of the biological sample and the solution of metal ions on the hydrophobic conductive nanostructures array grown on the three-integrated electrodes of exemplary biosensor 300 (step 404) may include passing or flowing the mixture of the biological sample and the solution of metal ions on the hydrophobic conductive nanostructures array grown on the three-integrated electrodes of exemplary biosensor 300. In a similar exemplary implementation, placing the mixture of the extracted lipid phase and the solution of metal ions on the hydrophobic conductive nanostructures array grown on the three-integrated electrodes of exemplary biosensor 300 (step 414) may include passing or flowing the mixture of the extracted lipid phase and the solution of metal ions on the hydrophobic conductive nanostructures array grown on the three-integrated electrodes of exemplary biosensor 300.

Figure 5:
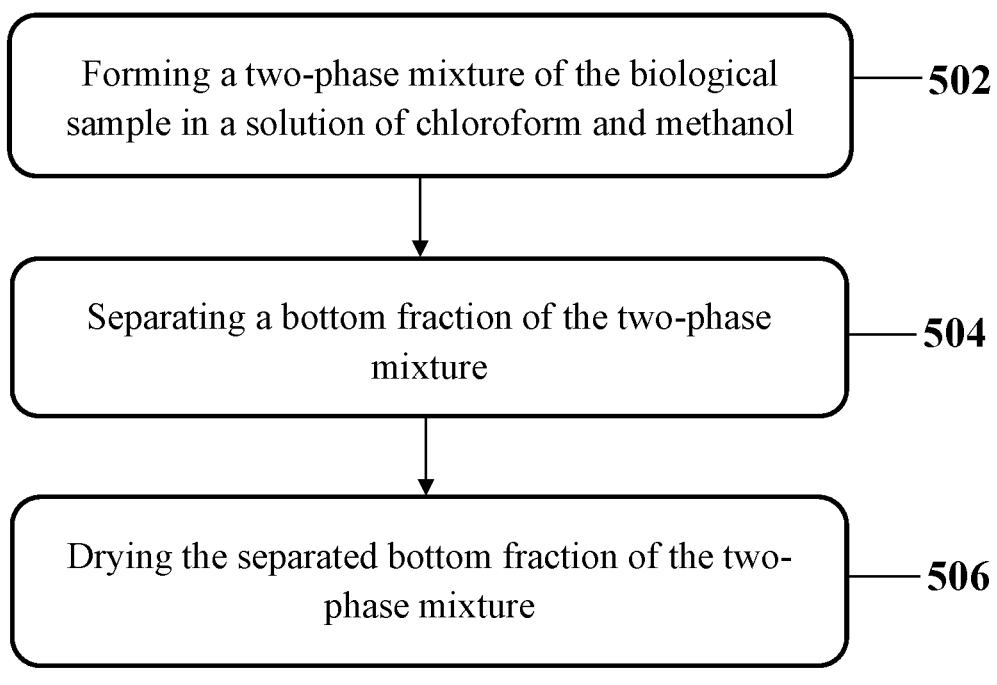
FIG. 5 shows an exemplary implementation of extracting lipid phase from an exemplary biological sample, consistent with one or more exemplary embodiments of the present disclosure.

FIG. 5 shows an exemplary implementation of extracting the lipid phase from the biological sample (step 410), consistent with one or more exemplary embodiments of the present disclosure. Accordingly, extracting the lipid phase from the biological sample (step 410) may include forming a two-phase mixture of the biological sample in a solution of chloroform and methanol (step 502), separating a bottom fraction of the two-phase mixture (step 504), and drying the separated bottom fraction of the two-phase mixture (step 506).

In an exemplary implementation, forming the two-phase mixture of the biological sample in the solution of chloroform and methanol (step 502) may include culturing the biological sample in a cell culture media, and adding a solution of chloroform and methanol to the cultured biological sample by adding an equal volume of the solution of chloroform and methanol with a volume ratio of 1:2 (Chloroform:methanol) to the biological sample; thereby, equal volumes of the solution of chloroform and methanol and the biological sample may be mixed together.

In another exemplary implementation, forming the two-phase mixture of the biological sample in the solution of chloroform and methanol (step 502) may include absorbing secretion of the biological sample by keeping the biological sample on a foam for a time period between 5 minutes and 30 minutes, forming a mixture of chloroform and the secretion of the biological sample by putting the foam containing the secretion of the biological sample in a chloroform solution inside a shaker for a time period between 5 minutes and 30 minutes, removing the foam the mixture of chloroform and the secretion of the biological sample, and adding methanol to mixture of chloroform and the secretion of the biological sample with a volume ratio of 1:2 (Chloroform:methanol).

As shown in FIG. 2, calculating the $R_{ct}$ of the EIS associated with the lipid secretion of the biological sample (step 102 of exemplary method 100) may further include recording the EIS of the dropped peripheral aqueous media of the biological sample on the array of hydrophobic conductive nanostructures using an electrochemical analyzer (step 206). In an exemplary implementation, recording the EIS of the dropped peripheral aqueous media of the biological sample on the array of hydrophobic conductive nanostructures using the electrochemical analyzer (step 206) may include connecting the three-integrated electrodes of exemplary biosensor 300 to the electrochemical analyzer, and recording the EIS from the dropped peripheral aqueous media of the biological sample on the array of hydrophobic conductive nanostructures. In an exemplary embodiment, the electrochemical analyzer may include a potentiostat device. In an exemplary implementation, recording the EIS from the dropped peripheral aqueous media of the biological sample on the array of hydrophobic conductive nanostructures may include recording the EIS from the dropped peripheral aqueous media of the biological sample on the array of hydrophobic conductive nanostructures at an AC voltage between about 5 mV and about 10 mV while sweeping a plurality of frequency values between about 0.01 Hz and about 100 kHz using the electrochemical analyzer.

Figure 6:
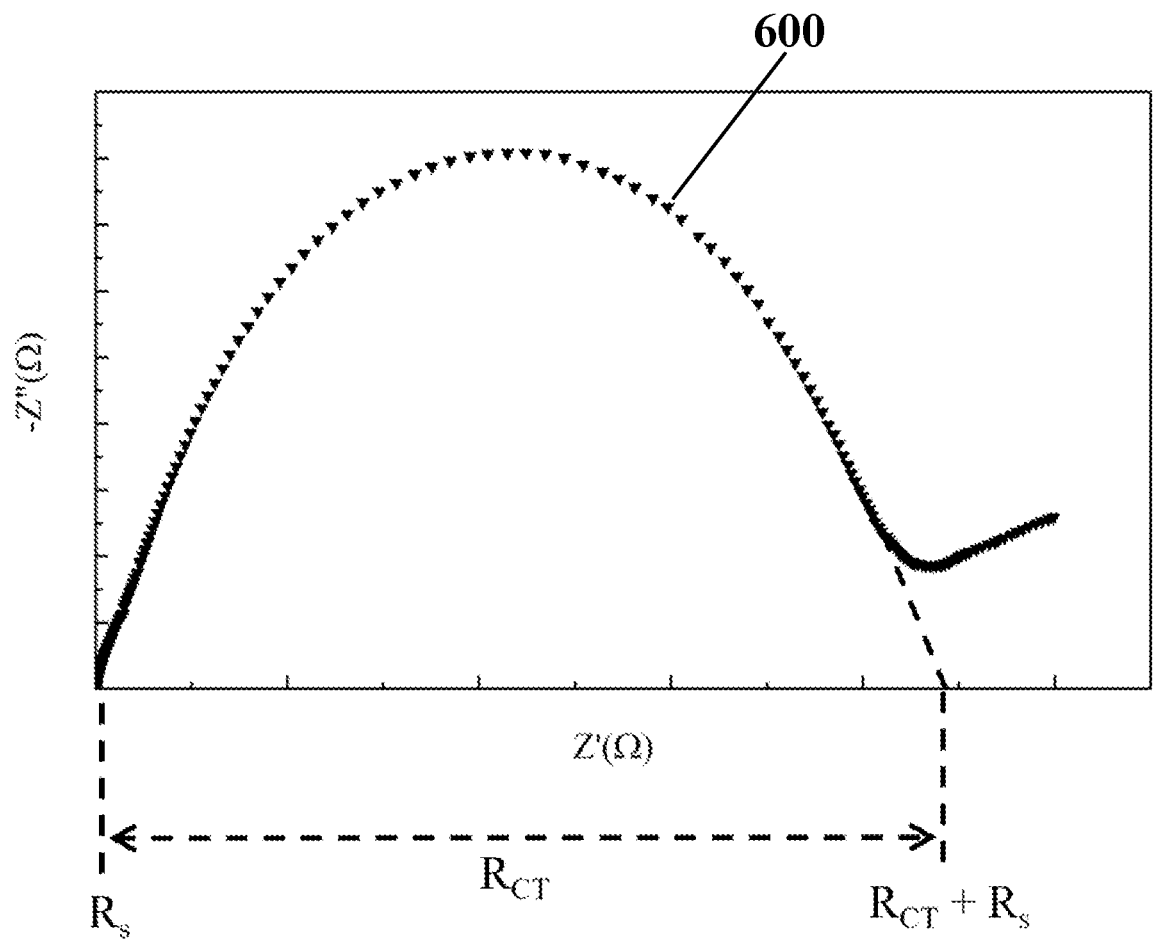
FIG. 6 illustrates a schematic view of an exemplary EIS recorded from the dropped peripheral aqueous media of the biological sample on the array of hydrophobic conductive nanostructures, consistent with one or more exemplary embodiments of the present disclosure.

In an exemplary implementation, recording the EIS from the dropped peripheral aqueous media of the biological sample on the array of hydrophobic conductive nanostructures may include recording a nyquist plot with a semicircular curve shape from the dropped peripheral aqueous media of the biological sample on the array of hydrophobic conductive nanostructures. FIG. 6 shows a schematic view of exemplary EIS 600 recorded from a dropped peripheral aqueous media of a biological sample on the array of hydrophobic conductive nanostructures, consistent with one or more exemplary embodiments of the present disclosure. Exemplary EIS 600 may include exemplary nyquist plot 600 with the semicircular curve shape including a set of recorded imaginary part of impedance ($Z''(\Omega)$) versus a set of recorded real part of impedance ($Z'(\Omega)$).

Referring to FIG. 2, calculating $R_{ct}$ of the EIS associated with the lipid secretion of the biological sample (step 102 of exemplary method 100) may further include measuring a diameter of a semicircular curve of the recorded EIS (step 208). Referring to FIG. 6, $R_{ct}$ may be measured as a diameter of a semicircular curve of exemplary EIS 600.

Referring again to FIG. 1, step 104 may include detecting a cancerous state for the biological sample if the calculated $R_{ct}$ that may be calculated utilizing step 102 is equal to or more than a threshold value. Moreover, step 106 may include detecting a normal (healthy) state for the biological sample if the calculated $R_{ct}$ that may be calculated utilizing step 102 is less than the threshold value. In an exemplary implementation, each of detecting the cancerous state for the biological sample (step 104) and detecting the normal state for the biological sample (step 106) may include comparing the calculated $R_{ct}$ with the threshold value.

In an exemplary implementation, the threshold value may be calculated by generating a dataset experimentally or clinically. In an exemplary implementation, generating the dataset may include generating a first set of $R_{ct}$ values that may be calculated from a plurality of normal (healthy) biological samples, generating a second set of $R_{ct}$ values that may be calculated from a plurality of cancerous biological samples, and selecting the threshold value that may include a $R_{ct}$ value at a border line between the first set of $R_{ct}$ values and the second set of $R_{ct}$ values.

In an exemplary implementation, the first set of $R_{ct}$ values and the second set of $R_{ct}$ values may be camculated utilizing exemplary process of step 102 for calculating the $R_{ct}$ of the EIS associated with lipid secretion of the biological sample described hereinabove. In an exemplary embodiment, the first set of $R_{ct}$ values may be calculated for a plurality of known normal (healthy) biological samples, for example, a plurality of healthy cell lines or patients. In an exemplary embodiment, the second set of $R_{ct}$ values may be calculated for a plurality of known cancerous biological samples, for example, a plurality of cancerous cell lines or patients.

In an exemplary implementation, generating the dataset may include generating the dataset as one of a calibration set of data, and a lookup table or plot. The dataset may be utilized to find the calculated $R_{ct}$ that may be calculated in exemplary step 102 there in order to distinguish that the calculated $R_{ct}$ is equal to, more than, or less than the threshold value; thereby, resulting in detecting a cancerous state or a normal state for the biological sample (steps 104 and 106). As a result, the cancerous status of the biological sample may be detected by comparing the calculated $R_{ct}$ with the threshold value that may include one of detecting a cancerous state for a biological sample if the calculated $R_{ct}$ is equal to or more than the threshold value, and detecting a normal (healthy) state for the biological sample if the calculated $R_{ct}$ is less than the threshold value.

Example 1: Fabrication of the Biosensor

In this example, an exemplary biosensor similar to biosensor 300 was fabricated. The fabrication process of the device was started by coating a glass substrate with a thermally grown Ni layer, followed by patterning three electrodes similar to exemplary electrodes 304, 306, and 308 using standard photolithography. Then, the exemplary biosensor was placed in a direct-current plasma enhanced chemical vapor deposition (DC-PECVD) reactor to grow vertically aligned multi-walled carbon nanotubes (VAMWCNTs) on surface of the exemplary patterned three electrodes.

Figure 7:
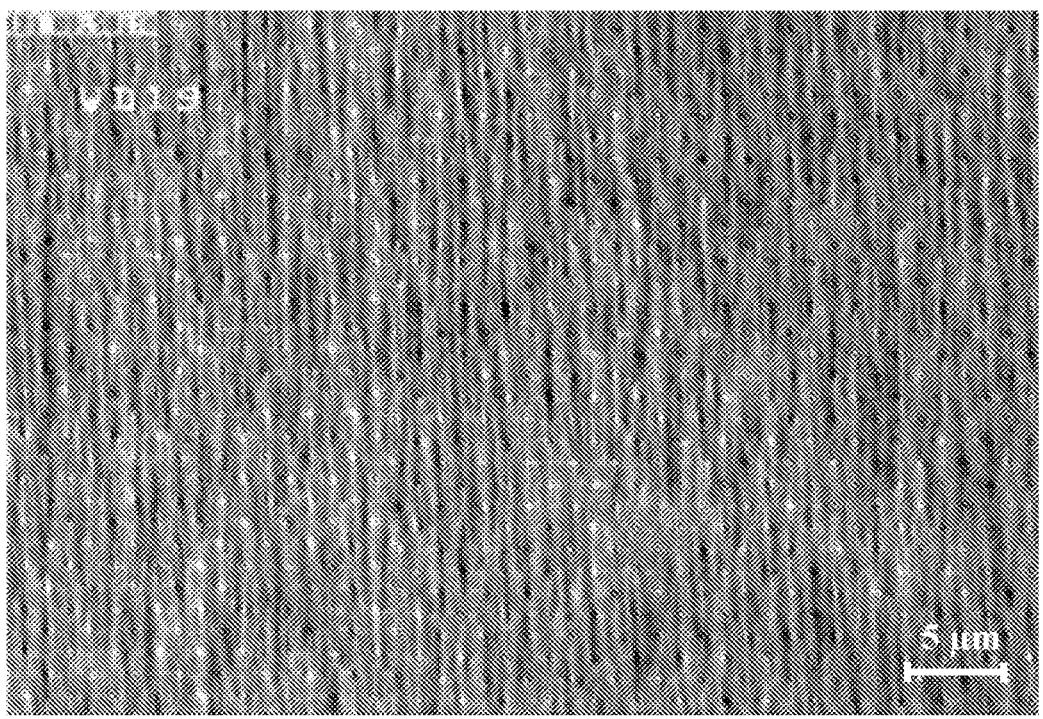
FIG. 7 illustrates a scanning electron microscopy (SEM) image of an exemplary array of vertically aligned multi-walled carbon nanotubes (VAMWCNTs) grown on exemplary three-integrated electrodes of an exemplary fabricated biosensor, consistent with one or more exemplary embodiments of the present disclosure.

FIG. 7 shows a scanning electron microscopy (SEM) image of exemplary array of VAMWCNTs grown on exemplary three-integrated electrodes of the exemplary fabricated biosensor, consistent with one or more exemplary embodiments of the present disclosure. It may be observed that each CNT beam of the VAMWCNTs array may have a length range between about 2 μm and about 12 μm, and a diameter range between about 20 nm and about 75 nm. Highly ordered CNTs as seen in FIG. 7 may be achieved as described above with a desired pattern and geometry.

Figure 8:
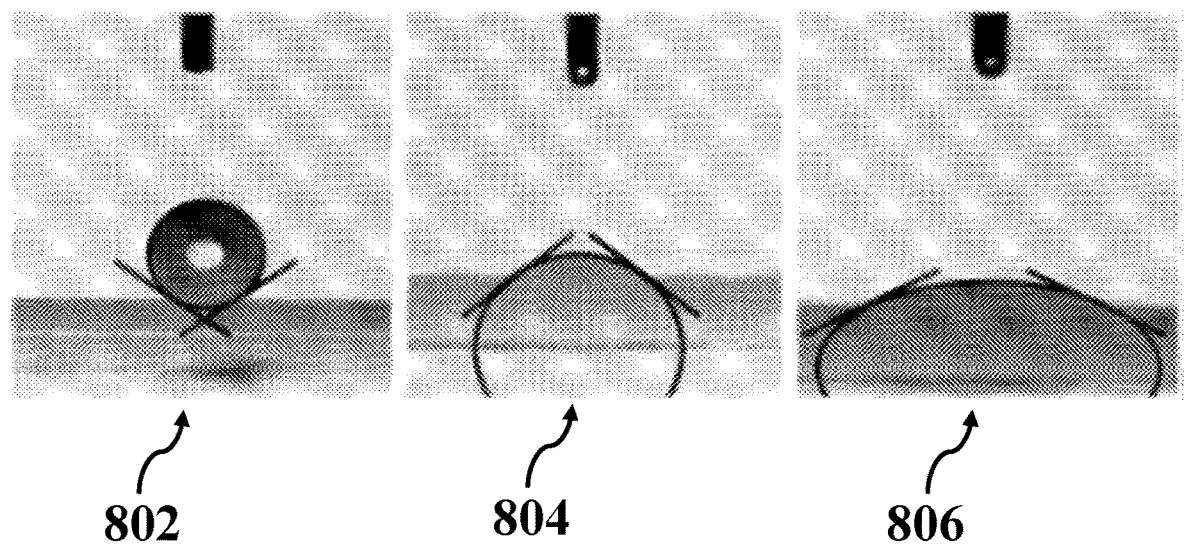
FIG. 8 illustrates contact angle measurement of an exemplary surface of VAMWCNTs for exemplary droplets of lipid free DMEM, DMEM containing about 10% lipid, and DMEM containing about 20% lipid, consistent with one or more exemplary embodiments of the present disclosure.

Super hydrophobic surface of CNT electrodes was analyzed by contact angle method for Dulbecco's Modified Eagle's medium (DMEM) cell culture media. FIG. 8 shows contact angle measurement of an exemplary surface of VAMWCNTs for exemplary droplets of lipid free DMEM (image 802), DMEM containing about 10% lipid (image 804), and DMEM containing about 20% lipid (image 806), consistent with one or more exemplary embodiments of the present disclosure. These images may reveal the super hydrophobic surface of MWCNTs structure as the contact angle (the droplet forming angle) was about 146° for lipid free DMEM without any fetal bovine serum (FBS) (image 802) meanwhile the contact angle in lipid contained (concentration of about 10%) DMEM solution was reduced to about 37° (image 804). Increasing the lipid concentration to about 20% resulted in efficient spreading of the droplet with a contact angle of about 25° (image 806). Such extended spreading of the lipid contained solution on the MWCNTs may present the usefulness of the CNTs (with hydrophobic surface) for lipid based dielectric measurements of the exemplary solution.

Example 2: Electrical Impedance Spectroscopy (Eis) of Cellular Secretion

Electrical impedance spectroscopy (EIS) of cellular secretion was carried out on the media of normal (MCF-10A), low grade cancerous (MCF-7), and high grade malignant (MDA-MB 231 and MDA-MB 468) breast cell lines cultured with similar concentration and vital cycles as analyzed by ANXV/PI technique. Table 1 shows results of the ANXV/PI analysis for the exemplary used cell lines whose secretion was used for lipid analysis. ANXV/PI results shows that concentration of the cells before investigating their media was about $3\times10^5$ cells/well with the total volume of about 1 ml. Moreover, about 88% of the cells from each type were in a live cycle meanwhile just less than about 8% were in necrosis. It is observable from Table 1 that all of the cells showed similar vital cycles before removal of their secretions.

TABLE 1

Results of the ANXV/PI analysis for MCF-10A, MCF-7, MDA-MB 231, and MDA-MB 468 breast cell lines.

| Cell Line | MCF-10A (%) | MCF-7 (%) | MDA-MB-231 (%) | MDA-MB-468 (%) |
|---|---|---|---|---|
| Live Cell | 88.4 ± 2.1 | 88.8 ± 2.2 | 88.5 ± 1.8 | 89.5 ± 1.0 |
| Early-Apoptosis | 1.69 ± 0.3 | 2.02 ± 0.23 | 2.11 ± 0.34 | 3.26 ± 0.25 |
| Late-Apoptosis | 1.75 ± 0.28 | 1.87 ± 0.09 | 3.33 ± 0.36 | 4.07 ± 0.41 |
| Necrosis | 8.15 ± 0.41 | 7.27 ± 0.39 | 6.03 ± 0.67 | 3.20 ± 0.88 |
| Count | 294559 ± 5514 | 295840 ± 6177 | 295912 ± 5106 | 296947 ± 4991 |

Cell Culture:

Cell lines (except MCF-10A) were kept in Dulbecco's modification of Eagle medium (DMEM) culture medium complimented with about 5% fetal bovine serum and about 1% penicillin/streptomycin at about 37° C. (about 5% $CO_2$, about 95% filtered air). MCF-10A was maintained in DMEM culture medium supplemented with about 5% horse serum, about 100 μg/ml EGF, about 1 mg/ml hydrocortisone, about 1 mg/ml cholera toxin, about 10 mg/ml insulin and about 1% penicillin/streptomycin.

EIS of the secretions of the cell lines was carried out by the exemplary fabricated biosensor similar to exemplary biosensor 300 at about 10 mV AC voltage sweeping the frequency from about 0.01 Hz to about 100 kHz at 255 points. The EIS response was recorded using portable electrochemical analyzer in three-electrode electrochemical impedance spectroscopy (EIS) mode. In order to carry out the dielectric spectroscopy on cellular secretion, the lipid extracted from similar concentration of cell lines or the whole cell culture media for cell lines were mixed by about 0.25 ml of potassium ferricyanide ($K_3Fe(CN)_6$) and flown (placed) on exemplary VAMWCNTs covered fabricated integrated sensor. The electrodes were calibrated using $K_3Fe(CN)_6$.

Figure 9:
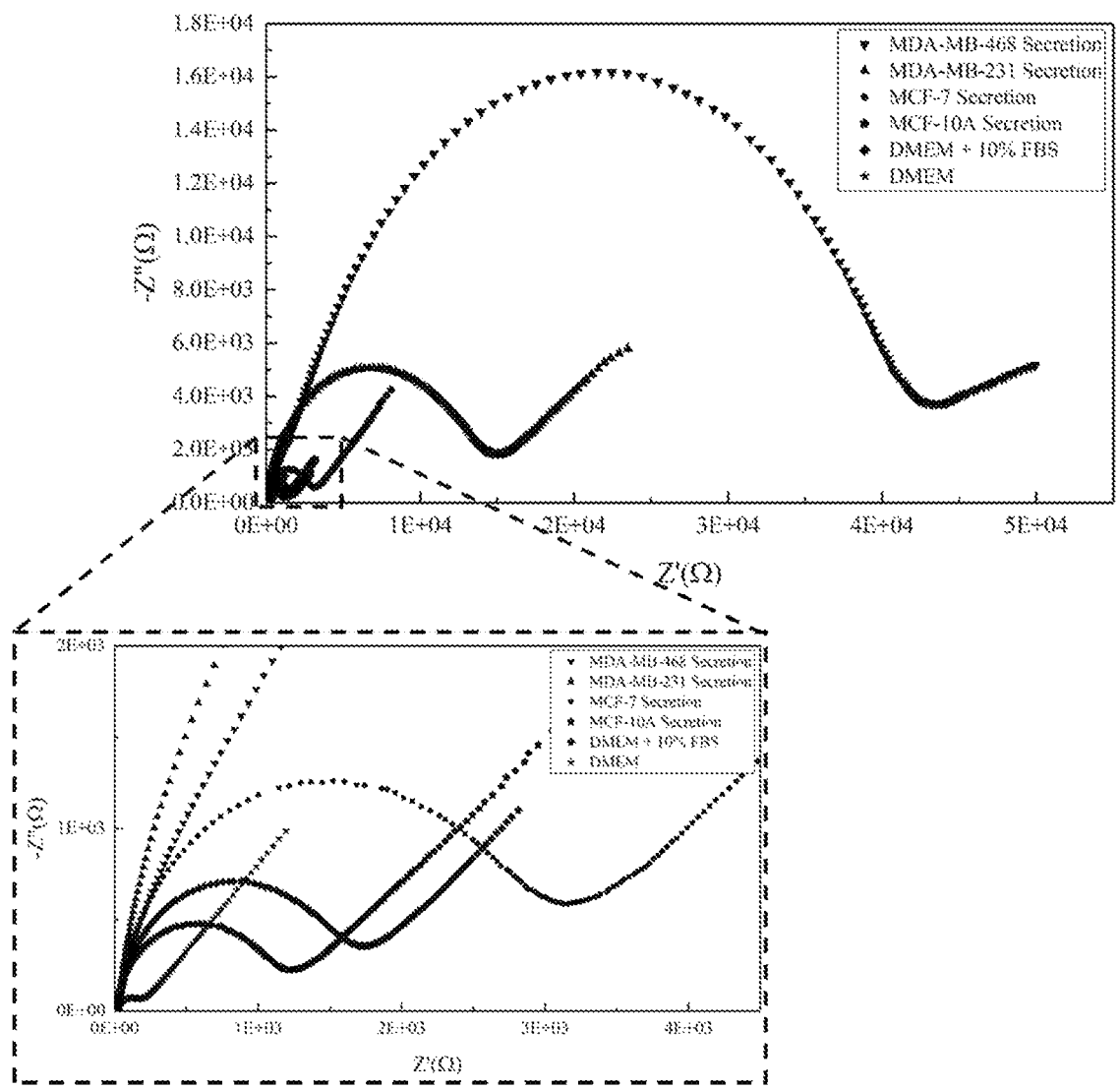
FIG. 9 illustrates the EIS results of cellular secretions for various breast cell lines and DMEM media as a control sample, consistent with one or more exemplary embodiments of the present disclosure.

FIG. 9 shows the EIS results of cellular secretions for various breast cell lines and DMEM media as a control sample, consistent with one or more exemplary embodiments of the present disclosure. The diameter of semicircular curves (as an indication of charge transfer resistance ($R_{ct}$) related to current blocking ability of dielectric (lipid) content of the solution), was observably greater in secretomes of malignant cells (MDA-MB 231 and MDA-MB 468) compared to non-metastatic and normal cells (MCF-7 and MCF-10A).

Furthermore, the lipid free EIS responses of the secretions from all cellular phenotypes, in which the lipid content of the solutions was selectively removed by an exemplary process similar to step 410 of method 100 described hereinabove, were recorded. Both lipid contained and lipid free samples were mixed by about 0.25 ml of $K_3Fe(CN)_6$ before recording the EIS responses. $K_3Fe(CN)_6$ was used as an electrical background solution for electrical scanning.

Figure 10:
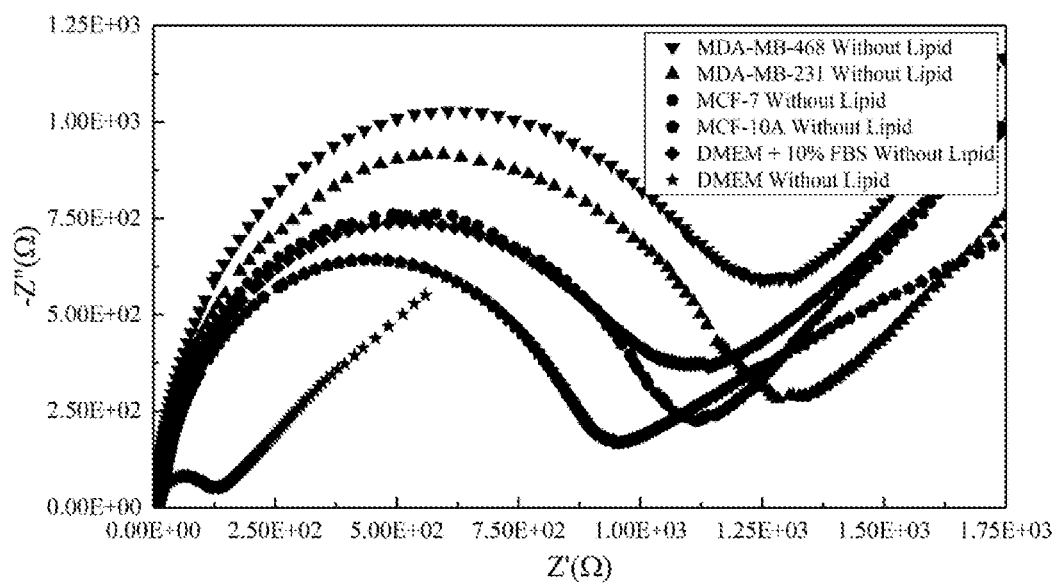
FIG. 10 illustrates the EIS results of lipid free parts of the secretion obtained from various breast cell lines and DMEM media as a control sample, consistent with one or more exemplary embodiments of the present disclosure.

FIG. 10 shows the EIS results of lipid free parts of the secretion obtained from various breast cell lines and DMEM media as a control sample, consistent with one or more exemplary embodiments of the present disclosure. It may be observed that EIS responses for lipid free cellular samples were mostly similar to each other, whereas EIS responses for lipid contained cellular samples as shown in FIG. 9 differ from each other significantly.

Table 2 shows comparative values of $R_{ct}$ for whole secretion and lipid free parts of the secretion for breast cell lines and DMEM culture media as control samples. $R_{ct}$ in the total secretion of cancer cells is more than $R_{ct}$ in the total secretion normal cells meanwhile the lipid free parts of all secretions exhibit similar $R_{ct}$ values. The $R_{ct}$ values for cancerous cell lines, and especially for metastatic cell lines are much higher than $R_{ct}$ values for normal cell lines or low-grade cancerous cell lines. This reveals that the secretion of malignant breast cells contain significant amounts of electrically insulator dielectric materials (lipid component). Accordingly, dielectric responses of lipid free secretions are similar in all of cell lines.

TABLE 2

Comparative values of $R_{ct}$ for whole secretion and lipid free parts of the secretion for breast cell lines and DMEM culture media as control samples.

| Sample | $R_{CT}$, Cell Media (KΩ) | $R_{CT}$, Without Lipid (KΩ) |
|---|---|---|
| DMEM | 0.15 ± 0.01 | 0.14 ± 0.01 |
| DMEM + 10% FBS | 1.62 ± 0.01 | 1.08 ± 0.01 |
| MCF-10A | 1.12 ± 0.05 | 0.85 ± 0.01 |
| MCF-7 | 2.98 ± 0.05 | 1.12 ± 0.01 |
| MDA-MB-231 | 13.16 ± 0.11 | 1.26 ± 0.01 |
| MDA-MB-468 | 38.16 ± 1.0 | 1.45 ± 0.02 |

According to the results presented in FIGS. 9-10, and Table 2, it may be gleamed that just bioactive lipids of the secretions may play an important role in distinguishing responses of the EIS in the secretions of cancer cells. About one order of magnitude differences could be observed between the response of lipid free and lipid contained secretions of malignant breast cells while this difference is much lower in normal breast cells.

Figure 11:
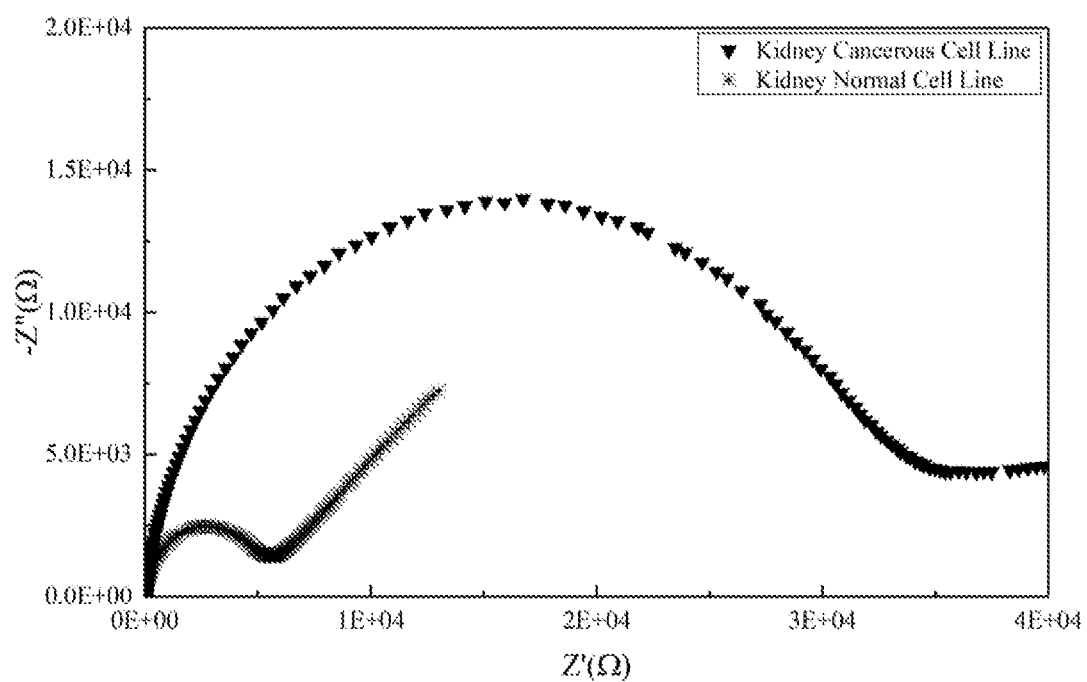
FIG. 11 illustrates the EIS results of normal and cancerous kidney cell lines, consistent with one or more exemplary embodiments of the present disclosure.
Figure 12:
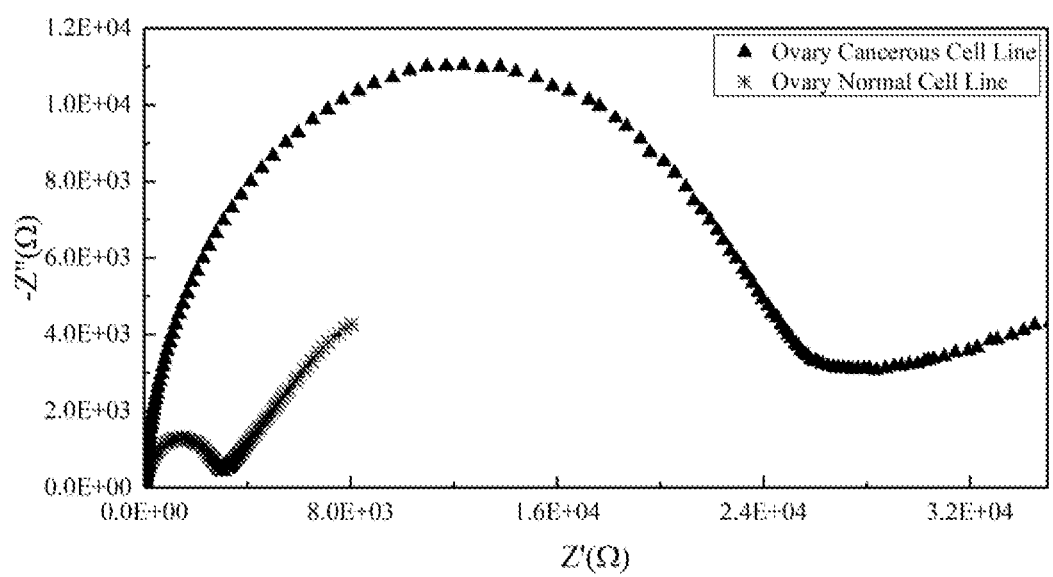
FIG. 12 illustrates the EIS results of normal and cancerous ovary cell lines, consistent with one or more exemplary embodiments of the present disclosure.
Figure 13:
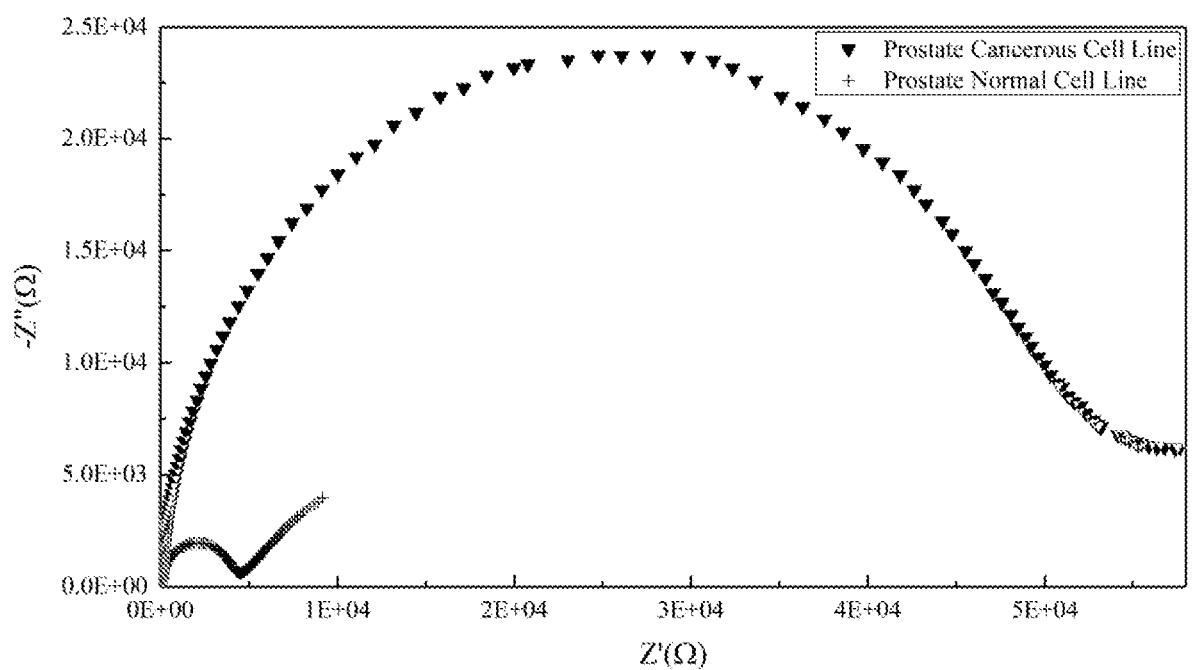
FIG. 13 illustrates the EIS results of normal and cancerous prostate cell lines, consistent with one or more exemplary embodiments of the present disclosure.
Figure 14:
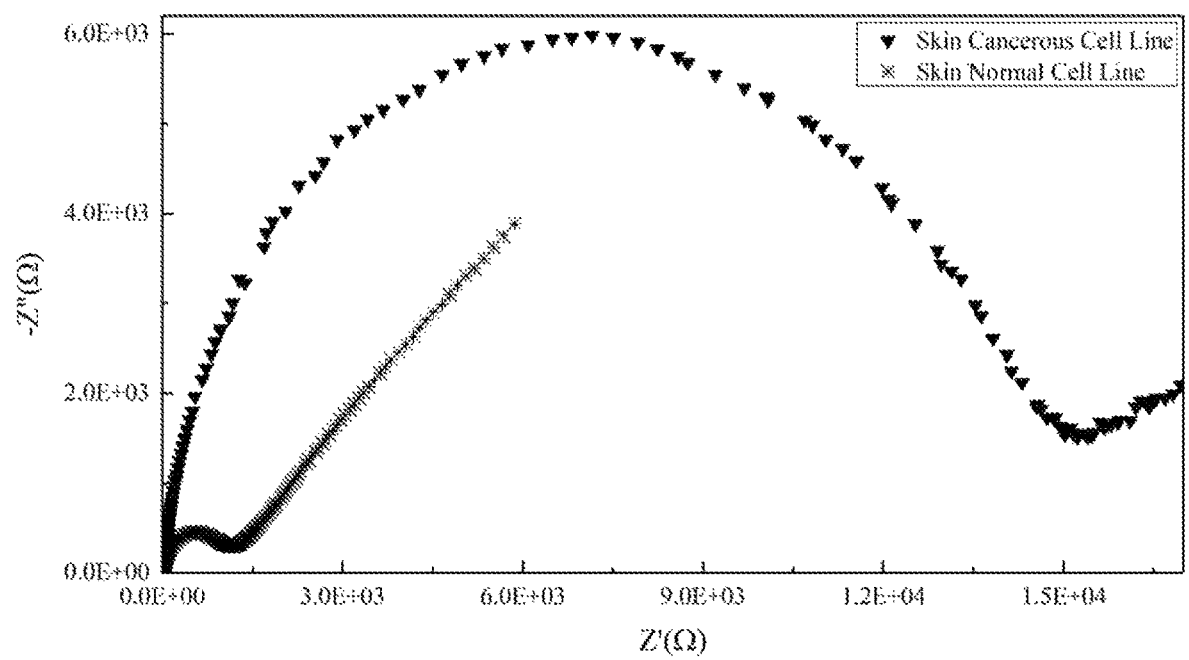
FIG. 14 illustrates the EIS results of normal and cancerous skin cell lines, consistent with one or more exemplary embodiments of the present disclosure.

Moreover, EIS was recorded for the secretions of both normal and cancerous types of kidney, ovary, prostate, and skin cell lines. FIG. 11 shows the EIS results of normal and cancerous kidney cell lines, consistent with one or more exemplary embodiments of the present disclosure. FIG. 12 shows the EIS results of normal and cancerous ovary cell lines, consistent with one or more exemplary embodiments of the present disclosure. FIG. 13 shows the EIS results of normal and cancerous prostate cell lines, consistent with one or more exemplary embodiments of the present disclosure. FIG. 14 shows the EIS results of normal and cancerous skin cell lines, consistent with one or more exemplary embodiments of the present disclosure. It may be seen from FIGS. 11-14 that presence of cancer cells in the cell line sample may be correlated with the indicated intensity of EIS peak. Cancerous samples may have intensified EIS peaks in comparison with normal (healthy) samples. Accordingly, a greater $R_{ct}$ value may be obtained for the cancerous samples compared with $R_{ct}$ value of normal samples.

Example 3: EIS Based Lipid Analysis of Clinical Biopsied Samples

To trace the probability of cancer involvement in clinical samples, the EIS of peripheral media fluid of samples resected by core needle biopsy (CNB) with similar sizes from more than 100 patients suspected to have breast cancer were recorded by the exemplary fabricated biosensor similar to exemplary biosensor 300 utilizing exemplary method 100. The secreted content of similar volumes of tissues were collected by a spongy foam and the lipids of the secretion were extracted. The extracted lipids were mixed by about 0.25 ml of $K_3Fe(CN)_6$ through the same protocol described for cell lines as described in EXAMPLE 2. The reference data for being a sample in cancerous or normal categories was standard hematoxylin and eosin (H&E) assay reported by a pathologist. So, a positive or negative score of each sample was due to the sample's histopathological results.

Figure 15:
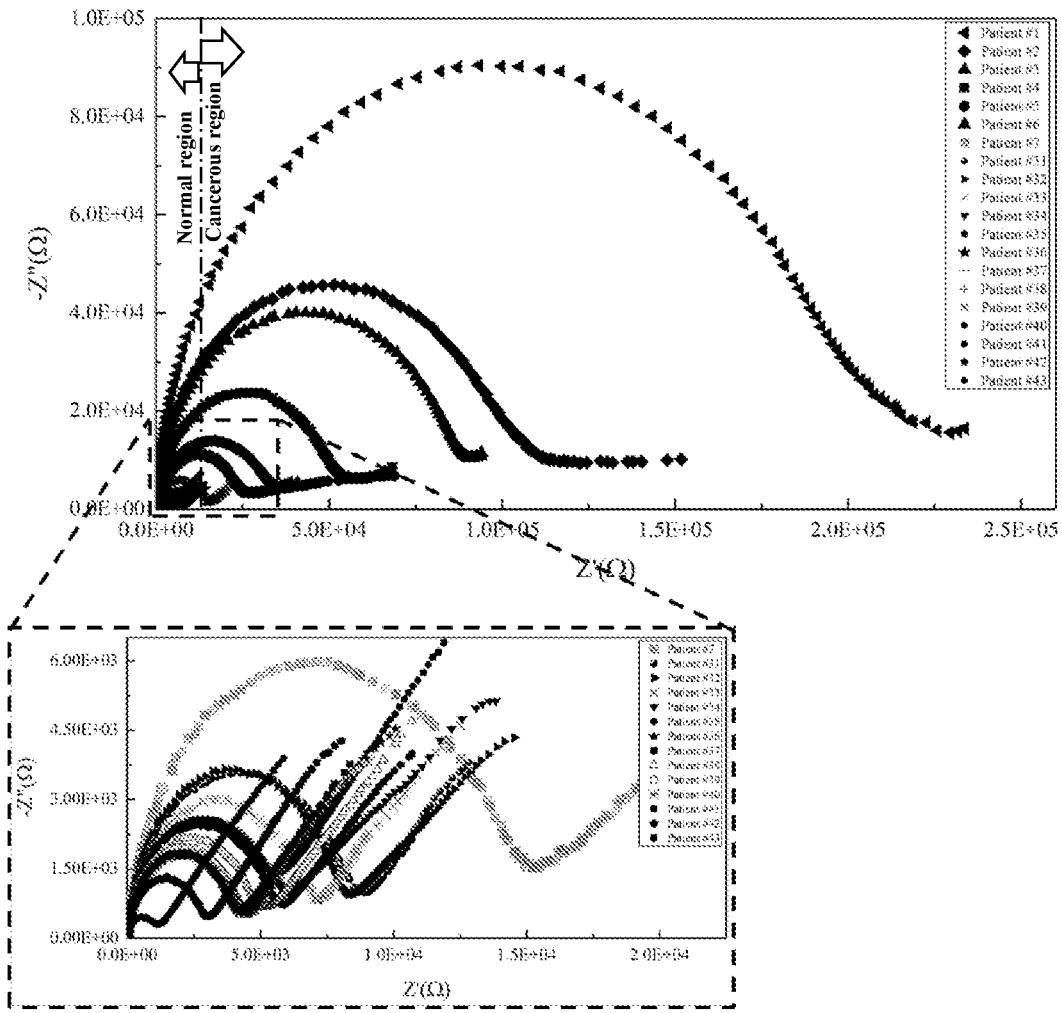
FIG. 15 illustrates the EIS results of biopsied samples from patients suspected to have breast cancer, consistent with one or more exemplary embodiments of the present disclosure.

FIG. 15 shows EIS results of biopsied samples from patients suspected to have breast cancer, consistent with one or more exemplary embodiments of the present disclosure. A significantly distinguished border may be observed in the $R_{ct}$ between normal (healthy) and cancer samples. Lipid content in secretion of cancerous samples exhibited one order of magnitude further $R_{ct}$ than normal samples (about $10^4$ versus about $10^3$). The nearest patients in cancer and normal states were cancer involved patient ID7 and normal patient ID31 that presented strongly distinguished EIS of secretion responses. The $R_{ct}$ for patient ID7 is about 14.8 kΩ and $R_{ct}$ for patient ID31 is about 7.91 kΩ.

Table 3 shows the comparative values of the EIS and histopathological results of the biopsied samples that were prepared with similar sizes from the 100 patients suspected to have breast cancer. No contrast was observed between EIS and H&E results in these patients. The $R_{ct}$ in the secretion of normally diagnosed samples (designated by negative sign in columns EIS Secretion Sensor and Pathological Diagnosis) was less than about 8 KΩ meanwhile $R_{ct}$ value is more than 14 KΩ in cancerous samples (designated by positive sign in columns EIS Secretion Sensor and Pathological Diagnosis). So, secretion of normal samples was categorized in a short range of $R_{ct}$ due to the rare concentration of lipid content in normal samples which may be in a range between 0 KΩ and 8 KΩ. Therefore, a threshold value for $R_{ct}$ equal to about 13 KΩ may be used as an appropriate criterion at a border line between cancerous region and normal region for analyzing biopsied samples suspected to have breast cancer in clinical tests. Accordingly, a biopsied sample with $R_{ct}$ value more than about 13 KΩ may be detected as a cancerous sample.

TABLE 3

EIS of secretion, H&E, tissue size and $R_{ct}$ results of breast biopsied samples (by CNB) prepared from 100 patients suspected to have breast cancer.

| Patient ID | EIS Secretion Sensor | Pathological Diagnosis | Size Sample ± 0.001 cm³ | $R_{CT}$ (KΩ) |
|---|---|---|---|---|
| 1 | + | + | 1.1 × 0.9 × 0.3 | 193 |
| 2 | + | + | 2.9 × 2.1 × 1.0 | 101.8 |
| 3 | + | + | 0.9 × 0.7 × 0.2 | 82.5 |
| 4 | + | + | 1.4 × 1.3 × 0.8 | 51.8 |
| 5 | + | + | 1.0 × 0.9 × 0.4 | 33.68 |
| 6 | + | + | 0.8 × 0.8 × 0.7 | 24.86 |
| 7 | + | + | 1.4 × 1.1 × 0.5 | 14.80 |
| 8 | + | + | 1.0 × 1.1 × 0.3 | 27.50 |
| 9 | + | + | 1.9 × 0.9 × 1.0 | 94.87 |
| 10 | + | + | 1.0 × 0.5 × 0.5 | 46.05 |
| 11 | + | + | 1.8 × 1.3 × 0.9 | 46.05 |
| 12 | + | + | 1.0 × 1.0 × 0.2 | 63.39 |
| 13 | + | + | 2.1 × 1.4 × 0.4 | 114.1 |
| 14 | + | + | 1.0 × 0.7 × 0.6 | 71.16 |
| 15 | + | + | 1.1 × 1.0 × 0.3 | 75.02 |
| 16 | + | + | 1.0 × 1.0 × 0.4 | 14.26 |
| 17 | + | + | 1.7 × 1.2 × 0.2 | 19.45 |
| 18 | + | + | 1.5 × 1.0 × 0.5 | 15.94 |
| 19 | + | + | 1.6 × 1.2 × 0.4 | 19.95 |
| 20 | + | + | 1.2 × 1.2 × 1.0 | 27.63 |
| 21 | + | + | 1.7 × 1.6 × 0.5 | 23.03 |
| 22 | + | + | 1.8 × 0.8 × 0.8 | 15.85 |
| 23 | + | + | 2.2 × 1.9 × 0.4 | 16.64 |
| 24 | + | + | 1.3 × 0.9 × 0.3 | 37.20 |
| 25 | + | + | 1.6 × 1.0 × 0.5 | 39.93 |
| 26 | + | + | 0.9 × 0.9 × 0.7 | 16.87 |
| 27 | + | + | 1.0 × 1.0 × 0.5 | 15.04 |
| 28 | + | + | 1.4 × 1.1 × 0.2 | 14.49 |
| 29 | + | + | 1.6 × 1.4 × 0.6 | 14.07 |
| 30 | + | + | 1.8 × 0.7 × 0.7 | 19.97 |
| 31 | − | − | 2.0 × 2.0 × 1.0 | 7.91 |
| 32 | − | − | 0.9 × 0.7 × 0.2 | 7.88 |
| 33 | − | − | 1.1 × 0.8 × 0.5 | 6.55 |
| 34 | − | − | 1.2 × 1.2 × 0.4 | 5.65 |
| 35 | − | − | 1.0 × 0.9 × 0.9 | 5.38 |
| 36 | − | − | 1.5 × 1.2 × 0.8 | 4.14 |
| 37 | − | − | 1.9 × 1.7 × 0.6 | 3.94 |
| 38 | − | − | 1.5 × 0.9 × 0.9 | 3.90 |
| 39 | − | − | 2.1 × 1.3 × 1.1 | 2.78 |
| 40 | − | − | 1.6 × 1.4 × 0.3 | 5.08 |
| 41 | − | − | 1.3 × 0.9 × 0.8 | 4.79 |
| 42 | − | − | 2.3 × 2.2 × 1.0 | 4.12 |
| 43 | − | − | 1.8 × 1.5 × 1.1 | 4.08 |
| 44 | − | − | 1.1 × 1.0 × 1.0 | 1.10 |
| 45 | − | − | 1.2 × 1.0 × 0.5 | 2.30 |
| 46 | − | − | 1.9 × 1.2 × 1.0 | 2.87 |
| 47 | − | − | 1.8 × 1.7 × 1.0 | 1.17 |
| 48 | − | − | 1.5 × 1.4 × 0.6 | 5.88 |
| 49 | − | − | 2.9 × 1.8 × 0.5 | 2.37 |
| 50 | − | − | 3.0 × 2.2 × 1.0 | 3.78 |
| 51 | − | − | 1.9 × 1.6 × 0.9 | 7.25 |
| 52 | − | − | 0.8 × 0.8 × 0.8 | 0.79 |
| 53 | − | − | 1.7 × 1.0 × 1.0 | 2.25 |
| 54 | − | − | 2.1 × 2.0 × 1.5 | 3.12 |
| 55 | − | − | 1.2 × 1.2 × 1.0 | 1.67 |
| 56 | − | − | 1.5 × 1.1 × 0.2 | 2.81 |
| 57 | − | − | 1.8 × 1.3 × 0.4 | 1.81 |
| 58 | − | − | 1.1 × 1.0 × 0.3 | 2.63 |
| 59 | − | − | 1.0 × 0.9 × 0.9 | 1.30 |
| 60 | − | − | 1.1 × 0.9 × 0.8 | 2.69 |
| 61 | − | − | 1.9 × 1.5 × 1.0 | 2.34 |
| 62 | − | − | 1.0 × 1.0 × 0.9 | 3.38 |
| 63 | − | − | 0.9 × 0.5 × 0.5 | 1.75 |
| 64 | − | − | 1.7 × 1.2 × 1.0 | 0.76 |
| 65 | − | − | 2.2 × 0.9 × 0.6 | 1.80 |
| 66 | − | − | 1.9 × 1.5 × 1.5 | 0.61 |
| 67 | − | − | 1.8 × 1.4 × 0.4 | 1.75 |
| 68 | − | − | 1.3 × 1.1 × 0.8 | 2.67 |
| 69 | − | − | 1.7 × 0.9 × 0.8 | 1.59 |
| 70 | − | − | 0.9 × 0.9 × 0.9 | 0.94 |
| 71 | − | − | 1.2 × 1.2 × 1.0 | 3.12 |
| 72 | − | − | 2.2 × 2.0 × 1.5 | 5.10 |
| 73 | − | − | 1.6 × 1.4 × 0.7 | 3.76 |
| 74 | − | − | 1.5 × 1.0 × 1.0 | 7.76 |
| 75 | − | − | 1.4 × 0.9 × 0.5 | 6.70 |
| 76 | − | − | 1.3 × 1.1 × 0.6 | 7.69 |
| 77 | − | − | 1.9 × 1.4 × 0.6 | 2.83 |
| 78 | − | − | 1.7 × 1.2 × 1.0 | 3.87 |
| 79 | − | − | 1.4 × 0.9 × 0.9 | 0.73 |
| 80 | − | − | 0.9 × 0.8 × 0.3 | 0.79 |
| 81 | − | − | 1.5 × 1.5 × 1.0 | 4.06 |
| 82 | − | − | 1.6 × 1.1 × 1.1 | 5.50 |
| 83 | − | − | 2.1 × 1.7 × 0.9 | 5.10 |
| 84 | − | − | 1.0 × 0.9 × 0.2 | 6.05 |
| 85 | − | − | 1.6 × 1.4 × 0.7 | 2.53 |
| 86 | − | − | 1.8 × 1.0 × 1.0 | 0.79 |
| 87 | − | − | 2.9 × 0.8 × 0.8 | 1.43 |
| 88 | − | − | 2.3 × 1.7 × 1.3 | 1.33 |
| 89 | − | − | 1.0 × 0.2 × 0.2 | 1.24 |
| 90 | − | − | 1.9 × 1.2 × 0.5 | 2.59 |
| 91 | − | − | 2.1 × 0.5 × 0.2 | 4.69 |
| 92 | − | − | 1.3 × 1.3 × 0.8 | 3.43 |
| 93 | − | − | 1.7 × 1.2 × 0.5 | 5.10 |
| 94 | − | − | 0.9 × 0.4 × 0.2 | 5.09 |
| 95 | − | − | 1.5 × 1.5 × 0.4 | 1.80 |
| 96 | − | − | 2.2 × 1.0 × 0.9 | 4.61 |
| 97 | − | − | 0.5 × 0.5 × 0.5 | 3.21 |
| 98 | − | − | 1.7 × 0.9 × 0.3 | 1.65 |
| 99 | − | − | 1.1 × 1.0 × 0.2 | 0.97 |
| 100 | − | − | 0.7 × 0.7 × 0.3 | 0.98 |

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for detecting cancerous status of a biological sample, comprising:
    growing an array of hydrophobic conductive nanostructures on three-integrated electrodes patterned on a catalyst layer deposited on a substrate, the hydrophobic conductive nanostructures comprising vertically aligned multi-walled carbon nanotubes (VAMWCNTs);
    putting lipid secretion of a biological sample in direct contact with the array of hydrophobic conductive nanostructures by dropping peripheral aqueous media of the biological sample on the array of hydrophobic conductive nanostructures grown on the three-integrated electrodes, the biological sample comprising a biological sample suspected to be cancerous, the peripheral aqueous media of the biological sample comprising the lipid secretion of the biological sample;
    recording an electrochemical impedance spectroscopy (EIS) associated with the lipid secretion of the biological sample from the dropped peripheral aqueous media of the biological sample on the array of hydrophobic conductive nanostructures at an AC voltage between 5 mV and 10 mV by sweeping a plurality of frequency values between 0.01 Hz and 100 kHz, the EIS comprising a semicircular curve;
    calculating a charge transfer resistance ($R_{ct}$) of the recorded EIS by measuring a diameter of the semicircular curve; and
    detecting a cancerous state for the biological sample, comprising:
        detecting a cancerous state for the biological sample if the calculated $R_{ct}$ is equal to or more than a threshold value of 10 KΩ; or
        detecting a normal state for the biological sample if the calculated $R_{ct}$ is less than the threshold value of 10 KΩ.

2. A method for detecting cancerous status of a biological sample, comprising:
    calculating a charge transfer resistance ($R_{ct}$) of an electrochemical impedance spectroscopy (EIS) associated with lipid secretion of a biological sample, the biological sample comprising a biological sample suspected to be cancerous, calculating the $R_{ct}$ of the EIS associated with the lipid secretion of the biological sample comprising:
        putting the lipid secretion of the biological sample in direct contact with an array of hydrophobic conductive nanostructures grown on three-integrated electrodes of a biosensor by dropping peripheral aqueous media of the biological sample on the array of hydrophobic conductive nanostructures, the peripheral aqueous media of the biological sample comprising the lipid secretion of the biological sample;
        recording the EIS of the lipid secretion of the biological sample being in direct contact with the array of hydrophobic conductive nanostructures using an electrochemical analyzer; and
        measuring a diameter of a semicircular curve of the recorded EIS; and
    detecting a cancerous state for the biological sample, comprising:
        detecting a cancerous state for the biological sample if the calculated $R_{ct}$ is equal to or more than a threshold value of 10 KΩ; or
        detecting a normal state for the biological sample if the calculated $R_{ct}$ is less than the threshold value of 10 KΩ.

3. The method of claim 2, wherein each of the detecting the cancerous state for the biological sample and the detecting the normal state for the biological sample comprises comparing the calculated $R_{ct}$ with the threshold value of 10 KΩ.

4. The method of claim 2, wherein dropping the peripheral aqueous media of the biological sample on the array of hydrophobic conductive nanostructures grown on the three-integrated electrodes of the biosensor comprises dropping the peripheral aqueous media of at least one of a plurality of biological cells, a plurality of biological cell lines, a part of a tissue obtained through surgery or biopsy, a lipid phase of the biological sample, and combinations thereof, on the array of hydrophobic conductive nanostructures grown on the three-integrated electrodes of the biosensor.

5. The method of claim 2, wherein dropping the peripheral aqueous media of the biological sample on the array of hydrophobic conductive nanostructures grown on the three-integrated electrodes of the biosensor comprises:
   forming a mixture of the biological sample and a solution of metal ions by mixing the biological sample with the solution of metal ions; and
   placing the mixture of the biological sample and the solution of metal ions on the hydrophobic conductive nanostructures array grown on the three-integrated electrodes of the biosensor.

6. The method of claim 2, wherein dropping the peripheral aqueous media of the biological sample on the array of hydrophobic conductive nanostructures grown on the three-integrated electrodes of the biosensor comprises dropping an extracted lipid phase of the biological sample on the array of hydrophobic conductive nanostructures grown on the three-integrated electrodes of the biosensor.

7. The method of claim 6, wherein dropping the peripheral aqueous media of the biological sample on the array of hydrophobic conductive nanostructures grown on the three-integrated electrodes of the biosensor comprises:
   extracting a lipid phase from the biological sample;
   forming a mixture of the extracted lipid phase and a solution of metal ions by mixing the extracted lipid phase with the solution of metal ions; and
   placing the mixture of the extracted lipid phase and the solution of metal ions on the hydrophobic conductive nanostructures array grown on the three-integrated electrodes of the biosensor.

8. The method of claim 7, wherein extracting the lipid phase from the biological sample comprises:
   forming a two-phase mixture of the biological sample in a solution of chloroform and methanol;
   separating a bottom fraction of the two-phase mixture; and
   drying the separated bottom fraction of the two-phase mixture.

9. The method of claim 8, wherein forming the two-phase mixture of the biological sample in the solution of chloroform and methanol comprises:
   culturing the biological sample in a cell culture media; and
   adding a solution of chloroform and methanol to the cultured biological sample by adding an equal volume of the solution of chloroform and methanol with a volume ratio of 1:2 (Chloroform:methanol) to the biological sample.

10. The method of claim 8, wherein forming the two-phase mixture of the biological sample in the solution of chloroform and methanol comprises:
    absorbing secretion of the biological sample by keeping the biological sample on a foam for a time period between 5 minutes and 30 minutes;
    forming a mixture of chloroform and the secretion of the biological sample by putting the foam containing the secretion of the biological sample in a chloroform solution inside a shaker for a time period between 5 minutes and 30 minutes;
    removing the foam from the mixture of chloroform and the secretion of the biological sample; and
    adding methanol to mixture of chloroform and the secretion of the biological sample with a volume ratio of 1:2 (Chloroform:methanol).

11. The method of claim 2, wherein dropping the peripheral aqueous media of the biological sample on the array of hydrophobic conductive nanostructures grown on the three-integrated electrodes of the biosensor comprises dropping the peripheral aqueous media of the biological sample on an array of vertically aligned multi-walled carbon nanotubes (VAMWCNTs) grown on the three-integrated electrodes of the biosensor.

12. The method of claim 11, wherein dropping the peripheral aqueous media of the biological sample on the array of VAMWCNTs grown on the three-integrated electrodes of the biosensor comprises dropping the peripheral aqueous media of the biological sample on the array of VAMWCNTs with a length between 2 μm and 12 μm and a diameter between 20 nm and 75 nm for each VAMWCNT of the array of VAMWCNTs.

13. The method of claim 2, wherein recording the EIS of the dropped peripheral aqueous media of the biological sample on the array of hydrophobic conductive nanostructures using the electrochemical analyzer comprises recording the EIS from the dropped peripheral aqueous media of the biological sample on the array of hydrophobic conductive nanostructures at a AC voltage between 5 mV and 10 mV by sweeping a plurality of frequency values between 0.01 Hz and 100 kHz.

14. The method of claim 2, wherein the electrochemical analyzer comprises a potentiostat.

15. The method of claim 2, further comprising fabricating the biosensor by growing the array of hydrophobic conductive nanostructures on the three-integrated electrodes patterned on a catalyst layer deposited on a substrate.

16. The method of claim 15, wherein:
    the substrate comprises at least one of a glass substrate, a silicon substrate, a ceramic substrate, and combinations thereof, and
    the catalyst layer comprises a layer of at least one of iron, cobalt, nickel, and combinations thereof.

17. The method of claim 15, wherein fabricating the biosensor comprises:
    depositing the catalyst layer on the substrate by thermally growing the catalyst layer on the substrate;
    patterning the three-integrated electrodes on the catalyst layer using photolithography technique, the three-integrated electrodes comprising a working electrode, a counter electrode, and a reference electrode; and
    growing the array of hydrophobic conductive nanostructures on the patterned three-integrated electrodes using a direct-current plasma enhanced chemical vapor deposition (DC-PECVD) technique.

* * * * *